United States Patent
Lidgard et al.

(10) Patent No.: US 9,657,330 B2
(45) Date of Patent: *May 23, 2017

(54) SERIAL ISOLATION OF MULTIPLE DNA TARGETS FROM STOOL

(71) Applicant: Exact Sciences Corporation, Madison, WI (US)

(72) Inventors: Graham P. Lidgard, Madison, WI (US); Janelle J. Bruinsma, Madison, WI (US); Michael J. Domanico, Middleton, WI (US); Hemanth Shenoi, Verona, WI (US)

(73) Assignee: Exact Sciences Corporation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/327,951

(22) Filed: Jul. 10, 2014

(65) Prior Publication Data

US 2015/0010907 A1   Jan. 8, 2015

Related U.S. Application Data

(62) Division of application No. 13/469,999, filed on May 11, 2012, now Pat. No. 8,808,990.

(60) Provisional application No. 61/485,386, filed on May 12, 2011.

(51) Int. Cl.
C12Q 1/68        (2006.01)
G01N 33/53       (2006.01)
G01N 33/574      (2006.01)

(52) U.S. Cl.
CPC ....... C12Q 1/6806 (2013.01); G01N 33/5308 (2013.01); G01N 33/57419 (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,683,058 A | 7/1987 | Lyman et al. |
| 4,683,195 A | 7/1987 | Mullis et al. |
| 4,683,202 A | 7/1987 | Mullis |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,494,810 A | 2/1996 | Barany et al. |
| 5,508,169 A | 4/1996 | Deugau et al. |
| 5,624,802 A | 4/1997 | Urdea et al. |
| 5,639,611 A | 6/1997 | Wallace et al. |
| 5,647,990 A | 7/1997 | Vassarotti |
| 5,648,212 A | 7/1997 | Albertsen et al. |
| 5,660,988 A | 8/1997 | Duck et al. |
| 5,710,264 A | 1/1998 | Urdea et al. |
| 5,773,258 A | 6/1998 | Birch et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,221,655 B1 | 4/2001 | Fung et al. |
| 6,235,502 B1 | 5/2001 | Weissman et al. |
| 6,248,229 B1 | 6/2001 | Meade |
| 6,444,461 B1 | 9/2002 | Knapp et al. |
| 6,872,816 B1 | 3/2005 | Hall et al. |
| 6,992,182 B1 * | 1/2006 | Muller ............... C12Q 1/6806 435/91.5 |

(Continued)

FOREIGN PATENT DOCUMENTS

| | | |
|---|---|---|
| CN | 100368566 | 2/2008 |
| CN | 101307311 | 11/2008 |
| CN | 101935647 | 7/2012 |
| EP | 265244 | 4/1988 |
| JP | 2010-533851 | 10/2010 |

(Continued)

OTHER PUBLICATIONS

Whitney et al. (Enhanced Retrieval of DNA from Human Fecal Samples Results in Improved Performance of Colorectal Cancer Screening Test, JMD Nov. 2004, vol. 6, No. 4).*

Life Technologies (Frequently Asked Questions—Streptavidin-Coupled Dynabeads®, attached, available at http://www.lifetechnologies.com/us/en/home/brands/product-brand/dynal/streptavidin-coupled-dynabeads/dynabeads-streptavidin.html, Aug. 1, 2007).*

(Continued)

*Primary Examiner* — Aaron Priest
(74) *Attorney, Agent, or Firm* — Casimir Jones, S.C.; Mary Ann Brow

(57) ABSTRACT

Provided herein is technology relating to isolating nucleic acids. In particular, the technology relates to methods and kits for extracting multiple DNA targets from human stool samples.

9 Claims, 4 Drawing Sheets

(56) References Cited

U.S. PATENT DOCUMENTS

| | | | |
|---|---|---|---|
| 7,005,266 | B2 | 2/2006 | Sprenger-Haussels |
| 7,387,874 | B2 | 6/2008 | Gocke et al. |
| 7,662,594 | B2 | 2/2010 | Kong et al. |
| 7,931,920 | B2 | 4/2011 | Hillebrand |
| 8,530,228 | B2 | 9/2013 | Han et al. |
| 8,574,890 | B2 | 11/2013 | Icenhour et al. |
| 8,808,990 | B2 | 8/2014 | Lidgard et al. |
| 8,980,107 | B2 | 3/2015 | Domanico et al. |
| 8,993,341 | B2 | 3/2015 | Bruinsma et al. |
| 8,999,176 | B2 | 4/2015 | Domanico et al. |
| 9,000,146 | B2 | 4/2015 | Bruinsma et al. |
| 2001/0035375 | A1 | 11/2001 | Humicke-Smith |
| 2002/0164631 | A1* | 11/2002 | Shuber ................ C12Q 1/6806 435/6.14 |
| 2003/0013112 | A1* | 1/2003 | Sprenger Haussels ........... 435/6 |
| 2003/0173284 | A1 | 9/2003 | Baker |
| 2005/0026175 | A1 | 2/2005 | Link et al. |
| 2006/0172302 | A1 | 8/2006 | Hermansen et al. |
| 2006/0172331 | A1 | 8/2006 | Sprenger-Haussels |
| 2006/0270843 | A1 | 11/2006 | Hall et al. |
| 2007/0202525 | A1 | 8/2007 | Quake et al. |
| 2008/0299621 | A1 | 12/2008 | Tatnell et al. |
| 2009/0253142 | A1 | 10/2009 | Allawi et al. |
| 2010/0129828 | A1 | 5/2010 | Beaulieu et al. |
| 2010/0151456 | A1 | 6/2010 | Ataman-Onal et al. |
| 2011/0105346 | A1 | 5/2011 | Beattie et al. |
| 2012/0122088 | A1 | 5/2012 | Zou et al. |
| 2012/0122105 | A1 | 5/2012 | Oldham-Haltom et al. |
| 2012/0122106 | A1 | 5/2012 | Zou et al. |
| 2014/0193813 | A1 | 7/2014 | Bruinsma et al. |
| 2014/0194607 | A1 | 7/2014 | Lidgard et al. |
| 2014/0194608 | A1 | 7/2014 | Lidgard et al. |
| 2015/0284770 | A1 | 10/2015 | Bruinsma et al. |
| 2016/0130635 | A1 | 5/2016 | Bruinsma et al. |

FOREIGN PATENT DOCUMENTS

| | | | |
|---|---|---|---|
| JP | 2010-533853 | 10/2010 | |
| WO | WO 90/11345 | 10/1990 | |
| WO | WO 2004108925 | 12/2004 | |
| WO | WO 2005023091 | 3/2005 | |
| WO | WO 2008150826 | 12/2008 | |
| WO | WO 2010014970 | 2/2010 | |
| WO | WO 2010028382 | 3/2010 | |
| WO | WO 2010028382 A2 * | 3/2010 | ......... A61B 10/0038 |
| WO | WO 2011014970 | 2/2011 | |
| WO | WO 2012002887 | 1/2012 | |
| WO | WO 2012155072 | 11/2012 | |

OTHER PUBLICATIONS

Lund et al. (Assessment of methods for covalent binding of nucleic acids to magnetic beads, DynabeadsTM, and the characteristics of the bound nucleic acids in hybridization reactions, Nucleic Acids Res. Nov. 25, 1988; 16(22): 10861-10880).*
Sinclair (To Bead or Not to Bead: Applications of Magnetic Bead Technology, The Scientist, available at http://www.the-scientist.com/?articles.view/articleNo/18984/title/To-Bead-or-Not-To-Bead--Applications-of-Magnetic-Bead-Technology/, Jun. 22, 1998).*
Qiagen (QIAamp® DNA Stool Mini Kit Handbook, attached, Aug. 2001).*
Fotedar et al. (Laboratory Diagnostic Techniques for Entamoeba Species, Clin Microbiol Rev. Jul. 2007; 20(3): 511-532).*
Morgan et al. (Comparison of PCR and Microscopy for Detection of Cryptosporidium parvum in Human Fecal Specimens: Clinical Trial, J Clin Microbiol. Apr. 1998; 36(4): 995-998).*
Read (Recovery efficiencies of nucleic acid extraction kits as measured by quantitative LightCyclerTM PCR, Mol Pathol. Apr. 2001; 54(2): 86-90).*
Shankaranara et al. (A rapid and simplified procedure for isolating DNA from scat samples, Current Science 75(9):883 (1998)).*
Qbiogene (GeneClean Kit, attached, Aug. 15, 2003).*
Ahlquist et al., "HemoQuant, a new quantitative assay for fecal hemoglobin. Comparison with Hemoccoult," Ann Intern Med, 1984, 101:297-302.
Ahlquist et al., "Colorectal Cancer Screening by Detection of Altered Human DNA in Stool: Feasibility of a Multitarget Assay Panel," Gastroenterology, 2000, 119: 1219-1227.
Andreadis and Chrisey, "Use of immobilized PCR primers to generate covalently immobilized DNAs for in vitro transcription/translation reactions," Nucleic Acids Res, 2000, 28:e5, 8 pages.
Aquamira Technologies, "Some Important Words in Regards to Filter Ratings," retrieved Oct. 3, 2014.
Ballabio, et al., "Screening for steroid sulfatase (STS) gene deletions by multiplex DNA amplification," Human Genetics, 1990, 84(6): 571-573.
Barnay, "Genetic disease detection and DNA amplification using cloned thermostable ligase," Proc. Natl. Acad. Sci USA, 1991, 88:189-93.
Beaucage et al., "Deoxynucleoside phosphoramidites—A new class of key intermediates for deoxypolynucleotide synthesis," Tetrahedron Lett., 1981, 22: 1859-1862.
Berthelet et al., "Rapid, direct extraction of DNA from soils for PCR analysis using polyvinylpolypyrrolidone spin columns," FEMS Microbiology Letters, 1996, 138:17-22.
Brown et al., "Chemical synthesis and cloning of a tyrosine tRNA gene," Meth Enzymol., 1979, 68:109-151.
Bustin, "Absolute quantification of mRNA using real-time reverse transcription polymerase chain reaction assays," J. Molecular Endocrinology, 2000, 25:169-193.
Chamberlain et al., "Deletion screening of the Duchenne muscular dystrophy locus via multiplex DNA amplification," Nucleic Acids Research, 1988, 16(23):11141-11156.
Cullen et al., "Simple and rapid method for direct extraction of microbial DNA from soil for PCR", Soil Biology and Biochemistry, vol. 30, No. 8/9, 1998, pp. 983-993.
Don et al., "'Touchdown' PCR to circumvent spurious priming during gene amplification," Nucleic Acids Research, 1991, 19(14):4008.
Doulton USA, "Absolute Vs. Nominal Microns Pore Ratings," Retrieved Oct. 3, 2014, from http://doultonusa.com/HTML pages/absolute_vs_nominal_microns_rating.htm.
European Search Report dated Oct. 27, 2014, EP Patent Application No. 12782489.4, 9 pages.
Fotedar et al., "Laboratory Diagnostic Techniques for Entamoeba Species," Clinical Microbiology Reviews, 2007, 20(3):511-532.
Guilfoyle et al., "Ligation-mediated PCR amplification of specific fragments from a class-II restriction endonuclease total digest," Nucleic Acids Research, 1997, 25:1854-1858.
Haaf et al., "Polymers of N-vinylpyrrolidone: synthesis, characterization, and uses," Polymer J., 1985, 17(1):143-152.
Hall et al., "Sensitive detection of DNA polymorphisms by the serial invasive signal amplification reaction," PNAS, 2000, 97:8272.
Hayden et al., "Multiplex-Ready PCR: A new method for multiplexed SSR and SNP genotyping," BMC Genomics, 2008, 9:80.
Hecker et al., "High and low annealing temperatures increase both specificity and yield in touchdown and stepdown PCR," Biotechniques, 1996, 20(3):478-485.
Herman et al., "Methylation-specific PCR: a novel PCR assay for methylation status of CpG islands," PNAS, 1996, 93(13):9821-9826.
Higuchi et al., "A general method of in vitro preparation and specific mutagenesis of DNA fragments: study of protein and DNA interactions," Nucleic Acids Research, 1988, 16(15):7351-7367.
Higuchi et al.,"Kinetic PCR analysis: real-time monitoring of DNA amplification reactions," Biotechnology, 1993, 11:1026-1030.
Higuchi et al., "Simultaneous amplification and detection of specific DNA sequences," Biotechnology, 1992, 10:413-417.
Kalinina et al., "Nanoliter scale PCR with TaqMan detection," Nucleic Acids Research, 1997, 25:1999-2004.
Laboratory for Environmental Pathogens Research, Dept of Environmental Sciences, University of Toledo, "Polyvinylpyrrolidone (PVPP) cleanup of DNA samples," Dec. 2004, 2 pages.

(56) References Cited

OTHER PUBLICATIONS

Lenntech B.V., "Absolute rating vs. nominal rating for filters," www.lenntech.com/library/fine/absolute/absolute-nominal-filters. htm, retrieved Oct. 3, 2014, 1 page.

Lyamichev et al., "Polymorphism identification and quantitative detection of genomic DNA by invasive cleavage of oligonucleotide probes," Nat. Biotech., 1999, 17:292-296.

Mangiapan et al. "Sequence Capture-PCR Improves Detection of Mycobacterial DNA in Clinical Specimens," Journal of Clinical Microbiology, 1996, 34. p. 1209-1215.

Matteucci et al., "Synthesis of deoxyoligonucleotides on a polymer support," J Am Chem Soc., 1981, 103:3185-3191.

Morgan et al., "Comparison of PCR and microscopy for detection of Cryptosporidium parvum in human fecal specimens: Clinical trial.," J. Clin. Microbiol., 1998, 36(4):995.

Narang et al., "Improved phosphotriester method for the synthesis of gene fragments," Meth Enzymol., 1979, 68: 90-98.

Parham et al., "Specific Magnetic Bead-Based Capture of Genomic DNA from Clinical Samples: Application to the Detection of Group B Streptococci in Vaginal/Anal Swabs," Clinical Chemistry, 2007, 53:9, p. 1570-1576.

"PVP in Stool Samples," MadSci Network: Molecular Biology, Nov. 20, 2006.

Qiagen, QIAamp DNA Stool Mini Kit Handbook, Aug. 2001, 40 pages.

QIAamp® genomic DNA Kits, product information, Apr. 2008, 12 pages.

Rehmanji et al., "A novel stabilization of beer with Polyclar Brewbrite," MBAA TQ, 2002, 39(1):24-28.

Roux, "Using mismatched primer-template pairs in touchdown PCR," Biotechniques, 1994, 16(5):812-814.

Schouten et al., "Relative quantification of 40 nucleic acid sequences by multiplex ligation-dependent probe amplification," Nucleic Acids Research, 2002, 30(12): e57.

Shames et al., "Identification of widespread Heliobacter hepaticus infection in feces in commercial mouse colonies by culture and PCR assay," J. Clin. Mocrobiol, 1995, 33(11):2968-72.

Sigma-Aldrich Poly(vinylpolypyrrolidone) product information, retrieved Jun. 26, 2013, 2 pages.

St. John et al., "Rapid capture of DNA targets," BioTechniques, 2008, 44:259-264.

Stone et al., "Detection of rRNA from four respiratory pathogens using an automated Qbeta replicase assay," Mol Cell Probes, 1996, 10:359-370.

Stratagene, Gene Characterization Kits, product information, 1988, 2 pages.

Traverso et al., "Detection of Apc Mutations in Fecal DNA from Patients with Colorectal Tumors," N. Engl. J. Med., 2002, 346(5).

Triglia et al., "A procedure for in vitro amplification of DNA segments that lie outside the boundaries of known sequences," Nucleic Acids Res., 1988, 16:8186.

Verweij et al., "Detection and Identification of Entamoeba Species in Stool Samples by a Reverse Line Hybridization Assay," J Clin Microbiol., 2003, 41(11):5041-5045.

Vogelstein et al., "Digital PCR," PNAS, 1999, 96: 9236-41.

Weiner et al., "Kits and their unique role in molecular biology: a brief retrospective," Biotechniques, 2008, 44:701-704.

Whitney et al., "Enhanced Retrieval of DNA from Human Fecal Samples Results in Improved Performance of Colorectal Cancer Screening Test," JMD, 2004, 6(4).

International Search Report and Written Opinion, mailed Apr. 16, 2013, for International Patent IDS Filed PCT/US2012/037581, 21 pages.

Zhang et al., "An improved method for purifying genomic DNA from forest leaf litters and soil suitable for PCR", Journal of Soils and Sediments, 2009, vol. 9, No. 3, pp. 261-266.

Glockner et al., "Methylation of TFPI2 in stool DNA: a potential novel biomarker for the detection of colorectal cancer," Cancer Res. Jun. 1, 2009;69(11):4691-9.

Trochimchuk et al., "A comparison of DNA extraction and purification methods to detect *Escherichia coil* 0157:H7 in cattle manure," J Microbiol Methods, 2003, 54:165-175.

Ahlquist et al., "Next Generation Stool DNA Testing for Detection of Colorectal Neoplasia—Early Marker Evaluation", poster presented at Colorectal Cancer: Biology to Therapy, American Association for Cancer Research Conference, Philadelphia, PA Oct. 27-30, 2010, 1 page.

Ahlquist et al., "Next-generation stool DNA test accurately detects colorectal cancer and large adenomas." Gastroenterology, 2012, 142:248-56, 9 pages.

Flintstones™ Complete Gummies. (n. d.). Retrieved Feb. 17, 2017, from http://www.flintstonesvitamins.com/products/complete-vitamin-gummies/ , 1 page.

Said HM. Cell and Molecular Aspects of Human Intestinal Biotin Absorption. The Journal of Nutrition. 139(1):158-162 (2009), 5 pages.

Avidin-Biotin Interaction Thermo Fisher Scientific (world wide web dot thermofisher.com/us/en/home/life-science/protein-biology/protein-biology-learning-center/protein-biology-resource-library/pierce-protein-methods/avidin-biotin-interaction.html, 6 pages.

Barbesino, "The Unintended Consequences of Biotin Supplementation: Spurious Immunoassay Results Lead to Misdiagnoses" world wide web dot aacc.org/publications/cln/articles/2016/december/bench-matters-december-2016), 4 pages.

Haaf et al., "Polymers of N-Vinylpyrrolidone: Characterization and Uses" Synthesis,Polymer Journal, vol. 17, No. I, pp. 143-152 (1985), 10 pages.

Sigma-Aldrich Product Specification for PVP10, 1 page.

\* cited by examiner

A

Two sequential extractions, Gene V

B

| Sample | Extraction | Strands/µL |
|--------|------------|------------|
| Gene A | #1 | 2,020 |
|        | #2 | N/A |
| Gene V | #1 | 505 |
|        | #2 | N/A |

A  Gene A

B  Gene F

FIG. 3 (con't)
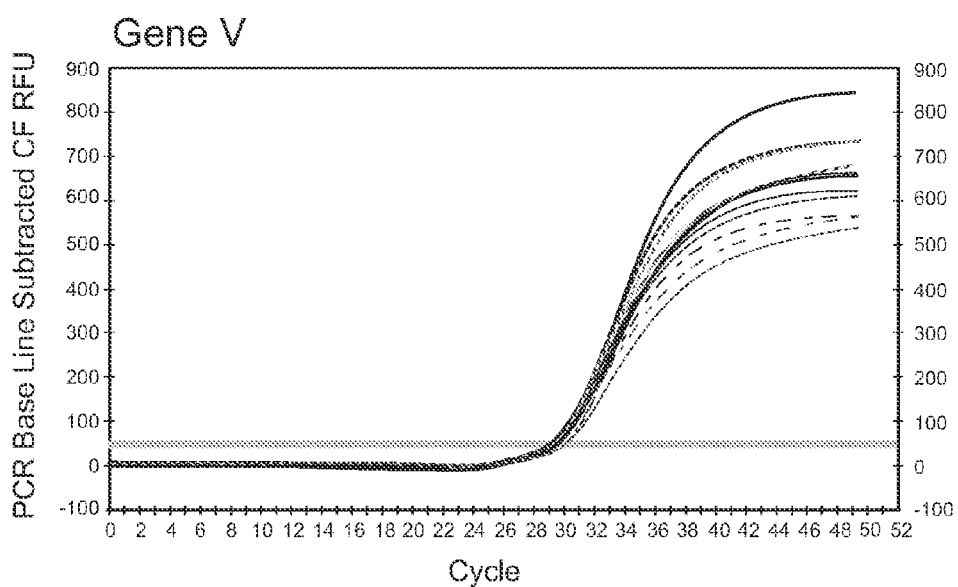
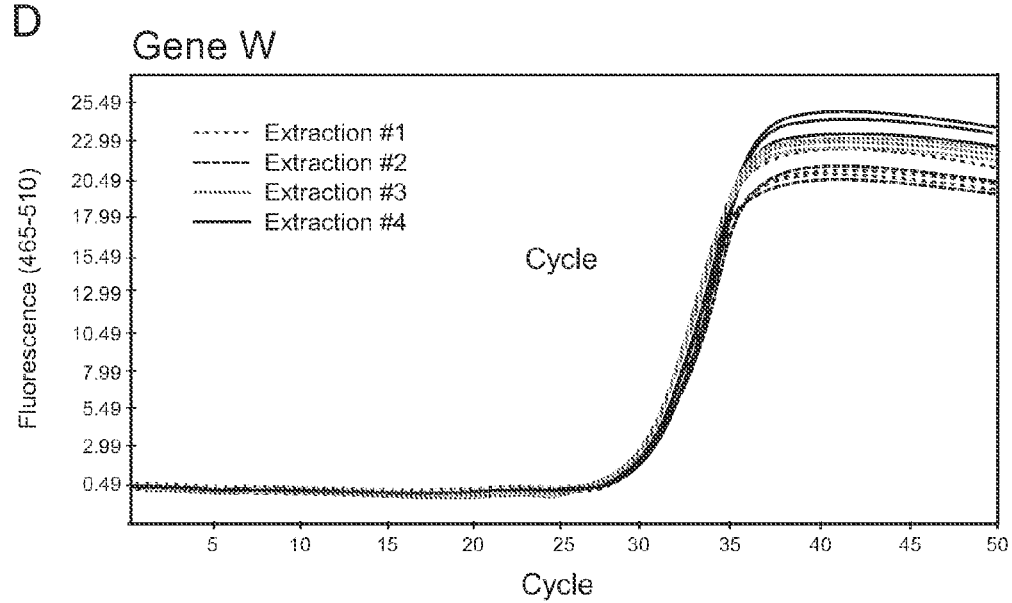

SERIAL ISOLATION OF MULTIPLE DNA TARGETS FROM STOOL

The present application is a divisional of U.S. patent application Ser. No. 13/469,999, filed May 11, 2012, which claims the benefit of U.S. Provisional Patent Application Ser. No. 61/485,386, filed May 12, 2011, each which is incorporated herein by reference in its entirety.

FIELD OF INVENTION

Provided herein is technology relating to isolating nucleic acids. In particular, the technology relates to methods and kits for extracting multiple DNA targets from human stool samples.

BACKGROUND

Isolating specific target nucleic acids from a sample is an important step for many medical diagnostic assays. For example, certain mutations and methylation states of particular genes are correlated, associated, and/or predictive of disease. DNA harboring these genes can be recovered from a sample and tested for the presence of the particular mutations and methylation states. While assaying an individual gene is informative, a more sensitive and specific diagnostic assay targets suites of genes comprising many members. Such an assay also provides additional information relating to the origin and stage of disease.

In practice, assaying such a multi-gene panel requires isolating and assaying several genetic targets from a sample. For many detection methods, detecting rare mutations or methylation events in a single gene requires isolating and testing a large quantity of DNA to obtain sufficient copies of the gene to allow detection of the rare event. This problem is compounded when assaying a panel of genes, each of which must be present in a large quantity for a robust diagnostic test. Thus, to detect rare mutations and methylation events in multiple genes, the isolated DNA must be highly concentrated and comprise a substantial portion of the detection assay. This requirement imposes many problems, however. For example, preparing such quantities and concentrations of DNA requires a large sample as input (i.e., having a mass of many grams), and thus requires a method that can prepare DNA from a large sample. In addition, assay inhibitors are often isolated and concentrated with the DNA preparation. Consequently, conventional assays that require concentrated DNA also often introduce inhibitory amounts of inhibitors into the assay. Moreover, if all targets of the panel are extracted and assayed simultaneously, the sensitivity of the assay is compromised because each gene of the panel composes a smaller fraction of the preparation as more targets are isolated. Also, if all members of the panel are extracted together and thus present in the same solution, the sensitivity of an assay directed to detecting any single particular target is compromised by interference from the non-target DNA molecules.

In addition, if a particular diagnostic target is present in a sample, it will be present in a small amount, thus providing a challenge for methods designed to detect it. For example, analyses of DNA from stool samples are complicated by the fact that large amounts of DNA from other sources are present. For example, bacteria compose approximately 60% of the dry mass of feces and the remainder is largely the remains of plant and animal matter ingested as food by the subject. As such, the human subject's cells, and only those that slough off the lining of the digestive tract, are a very small fraction of the stool. Furthermore, in assays to detect gene modifications indicative of colon cancer, if a cancerous tumor is present in the colon, then cells derived from that tumor would compose only a small fraction of the human subject's gut cells that slough off the digestive tract lining. Consequently, cancer cells (and the DNAs they contain) make up a minimal amount of the stool mass.

Conventional methods and kits for isolating DNA from samples typically prepare total DNA (i.e., non-specifically) from the sample. Consequently, total DNA isolated from a stool sample comprises DNA from the gut-resident bacteria (and any viruses, eukaryotes, and archaea present) along with DNA from the subject sampled. Moreover, conventional methods and kits are primarily designed to prepare DNA from small samples, e.g., samples having masses of less than 1 gram, e.g., 50 to 200 milligrams. Consequently, conventional methods are not applicable to high-sensitivity and high-specificity multi-gene panel analyses because they cannot prepare sufficient amounts of highly concentrated, inhibitor-free DNA from large samples such as a stool sample. Assays using DNA prepared with conventional methods will not provide a sample that can be assayed with the required sensitivity threshold for detecting rare mutation or methylation events. Using a conventional method or kit to provide the starting quantities needed to attain such sensitivity requires multiple DNA extractions (e.g., the use of multiple kits) from multiple samples in addition to extra purification steps to remove inhibitors. Therefore, what is needed is a method of preparing concentrated, inhibitor-free DNA from a sample for each member of a gene panel for use in diagnostic assays.

SUMMARY

Provided herein is technology relating to isolating nucleic acids. In particular, the technology relates to methods and kits for extracting multiple DNA targets from human stool samples. The DNA solutions produced are highly concentrated, i.e., have a large amount of DNA in a small volume, and contain minimal amounts of substances that inhibit downstream assays used to test the DNA. Accordingly, the technology provided herein finds use in assays that test multi-gene panels, particularly those that detect rare genetic events.

For example, provided herein are methods for isolating a nucleic acid from a stool sample comprising contacting a stool sample with a target-specific capture reagent; binding a target nucleic acid, when present, to the target-specific capture reagent to form a complex; isolating the complex comprising the target-specific capture reagent and the target nucleic acid, when present, from the stool sample; eluting the target nucleic acid, when present, from the complex to produce a target nucleic acid solution comprising the target nucleic acid, when present; and repeating the method using a different target-specific capture reagent. The methods are appropriate for large samples, e.g., having a mass of at least 4 grams. Moreover, each eluted target nucleic acid is sufficiently purified, sufficiently concentrated, and sufficiently free of inhibitors such that each eluted target nucleic acid, when present, is detected by a quantitative PCR when the target nucleic acid solution composes up to approximately one-third of a volume of the quantitative PCR.

In some embodiments of the methods provided, the target nucleic acid is a human target nucleic acid. In additional embodiments, the target nucleic acid is a DNA. While not limited in the means by which the nucleic acid is isolated from the stool sample, in some embodiments the target-specific capture reagent is a sequence-specific nucleic acid capture reagent. In some embodiments, the sequence-specific nucleic acid capture reagent is an oligonucleotide and in some embodiments the oligonucleotide is covalently attached to a magnetic or paramagnetic particle. Some embodiments provide that a magnet is used for the isolating step and some embodiments provide for the simultaneous isolation of more than one target using multiple target-specific capture reagents in a single isolation step.

The methods provided are applicable to many types of assays. For example, in some embodiments, the nucleic acid is an RNA and the quantitative PCR is a quantitative RT-PCR. As another example, in some embodiments the target nucleic acid is correlated with a disease state selected from the set consisting of colon cancer and adenoma.

Stool samples can be taken and prepared in many ways. For example, in some embodiments the stool sample comprises a stool supernatant prepared from a stool homogenate. In some embodiments the stool sample comprises a stool supernatant further treated with polyvinylpolypyrrolidone and guanidine thiocyanate. In some embodiments, the methods comprise exposing the stool sample to a condition that denatures nucleic acids before the contacting step. For example, some embodiments provide that the condition that denatures nucleic acids comprises heating at 90° C. for 10 minutes. Some embodiments further provide that the binding step comprises incubating at ambient temperature for 1 hour.

Provided herein are methods for the serial extraction of target nucleic acids from a stool sample. Accordingly, in embodiments of the methods the repeating step is performed n times to produce n+1 target nucleic acid solutions, each comprising, when present, a different target nucleic acid. For example, in some embodiments, n is at least 3.

Also provided are methods for isolating a target human DNA from a human stool sample comprising obtaining a stool sample from a human subject; homogenizing the stool sample in an homogenization buffer to produce an homogenized stool sample; preparing a stool supernatant from the homogenized stool sample; treating the stool supernatant with polyvinylpolypyrrolidone to produce a clarified stool supernatant; adding guanidine thiocyanate a volume of clarified stool supernatant to produce a solution comprising guanidine thiocyanate; heating the solution; adding to the solution a target-specific capture reagent comprising an oligonucleotide covalently attached to a paramagnetic or magnetic particle, wherein the oligonucleotide is complementary to the target human DNA; incubating the solution at ambient temperature to produce a complex comprising the target-specific capture reagent and the target human DNA, if present; exposing the solution to a magnetic field to isolate the complex from the solution; retaining the solution produced in the preceding step; eluting the target human DNA, if present, from the complex to produce a target nucleic acid solution comprising the target nucleic acid, when present; and repeating the heating, adding, incubating, exposing, retaining, and eluting steps of the method using a different target-specific capture reagent in the adding step and the solution retained in the retaining step, wherein each eluted target nucleic acid is sufficiently purified, sufficiently concentrated, and sufficiently free of inhibitors such that each eluted target human DNA, when present, is detected by a quantitative PCR when the target nucleic acid solution composes up to approximately one-third of a volume of the quantitative PCR. In some embodiments multiple target-specific capture reagents are added in the adding step.

In some embodiments the stool sample is at least 4 grams. In some embodiments the clarified stool supernatant comprises 2.0-3.0 M guanidine thiocyanate and in some embodiments the guanidine thiocyanate concentration is 2.4 M. In some embodiments the guanidine thiocyanate is added to 10 milliliters of clarified stool supernatant and in some embodiments the solution is heated to 90° C. for 10 minutes. In some embodiments, the target human DNA is from a gene associated with a disease state selected from the set consisting of colon cancer and adenoma. In some embodiments of the methods provided, the repeating step is performed n times to produce n+1 target nucleic acid solutions, each comprising, when present, a different target nucleic acid. For example, in some embodiments, n is at least 3.

Also provided herein are kits for isolating a target human DNA from a human stool sample comprising a volume of stool homogenization solution suitable for processing a human stool sample having a mass of at least 4 grams; a target-specific capture reagent comprising an oligonucleotide covalently attached to a paramagnetic or magnetic particle, wherein the oligonucleotide is complementary to the target human DNA; and an instruction for use, wherein the kit produces a solution comprising the target human DNA, when present, that is sufficiently purified, sufficiently concentrated, and sufficiently free of inhibitors such that the target human DNA, when present, is detected by a quantitative PCR when the solution composes up to approximately one-third of a volume of the quantitative PCR. In some embodiments of the kits, the kits further comprise a magnet. In some embodiments, the kits further comprise polyvinylpolypyrrolidone and in some embodiments the kits further comprise guanidine thiocyanate. In some embodiments, the kits further comprise an elution or wash solution.

In addition, provided herein are uses of a target-specific capture reagent comprising an oligonucleotide attached to a paramagnetic or magnetic particle; polyvinylpolypyrrolidone; guanidine thiocyanate; and a magnet for the manufacture of a kit for isolating a target human DNA from a human stool sample having a mass of at least 4 grams, wherein the kit produces a solution comprising the target human DNA, when present, that is sufficiently purified, sufficiently concentrated, and sufficiently free of inhibitors such that the target human DNA, when present, is detected by a quantitative PCR when the solution composes up to approximately one-third of a volume of the quantitative PCR.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

DETAILED DESCRIPTION

Figure 1:
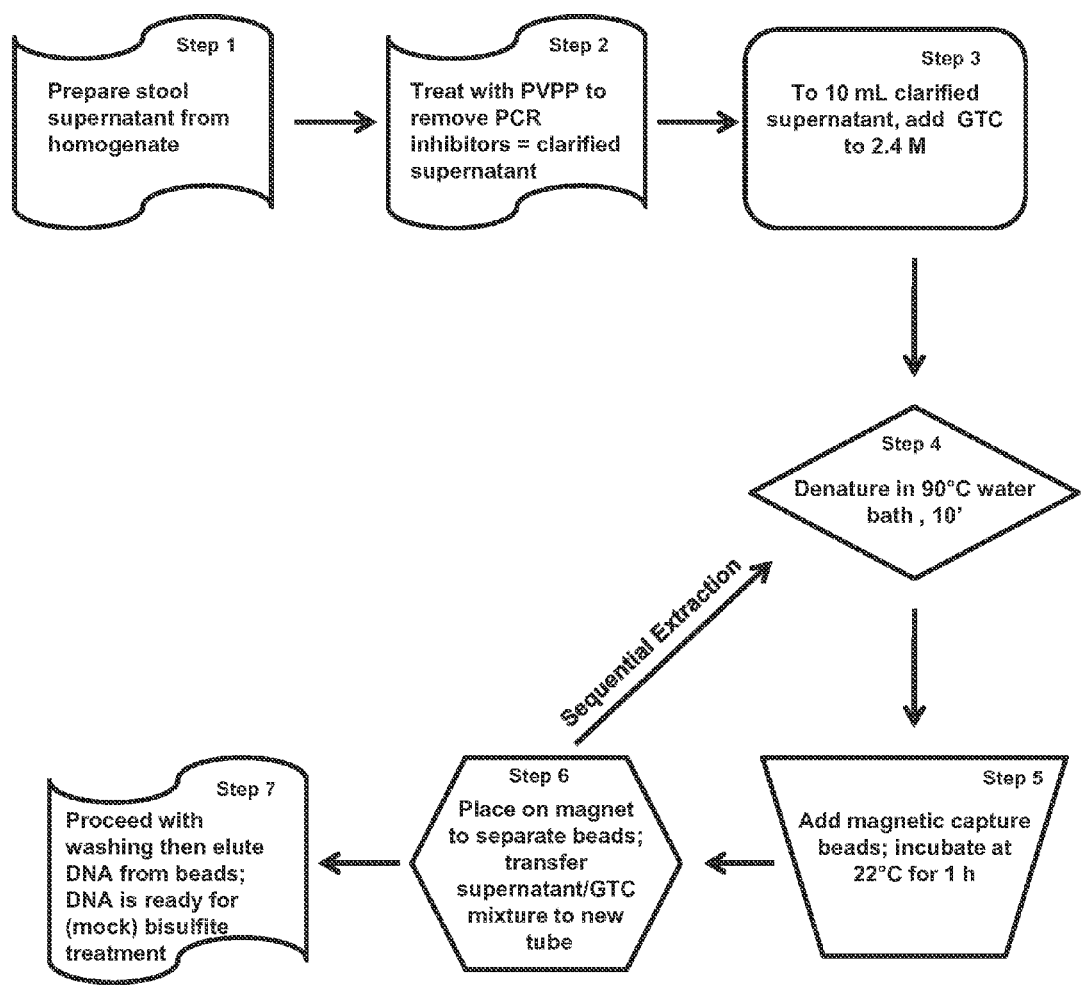
FIG. 1 is a flowchart of the sequential extraction process.

Provided herein is technology relating to isolating nucleic acids. In particular, the technology relates to methods and kits for extracting multiple DNA targets from human stool samples.

Accordingly, provided herein are methods for producing DNA samples from large samples that comprise inhibitors and in which the target DNA is in low abundance. In particular, the methods are directed to producing concentrated and highly purified DNA samples having a small volume (e.g., less than 100, and in some cases less than 60 microliters) and that are substantially and/or effectively free of substances that inhibit assays used to test the DNA samples (e.g., PCR, INVADER assay, etc.). Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value for the diagnosis and treatment of cancer.

Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances can compromise the accuracy and precision of these assays directed to detecting such low amounts of a target. Accordingly, provided herein are methods providing the requisite management of volume and concentration to produce such DNA samples.

DEFINITIONS

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, "a capture reagent" refers to any agent that is capable of binding to an analyte (e.g., a target). Preferably, "a capture reagent" refers to any agent that is capable of specifically binding to an analyte, e.g., having a higher binding affinity and/or specificity to the analyte than to any other moiety. Any moiety, such as a cell, a cellular organelle, an inorganic molecule, an organic molecule and a mixture or complex thereof can be used as a capture reagent if it has the requisite binding affinity and/or specificity to the analyte. The capture reagents can be peptides, proteins, e.g., antibodies or receptors, oligonucleotides, nucleic acids, vitamins, oligosaccharides, carbohydrates, lipids, small molecules, or a complex thereof. Capture reagents that comprise nucleic acids, e.g., oligonucleotides, may capture a nucleic acid target by sequence-specific hybridization (e.g., through the formation of conventional Watson-Crick basepairs), or through other binding interactions. When a capture oligonucleotide hybridizes to a target nucleic acid, hybridization may involve a portion of the oligonucleotide, or the complete oligonucleotide sequence, and the oligonucleotide may bind to a portion of or to the complete target nucleic acid sequence.

As used herein, the terms "subject" and "patient" refer to any animal, such as a dog, cat, bird, livestock, and particularly a mammal, preferably a human. In some instances, the subject is also a "user" (and thus the user is also the subject or patient).

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like. Environmental samples include environmental material such as surface matter, soil, mud, sludge, biofilms, water, crystals, and industrial samples. Such examples are not however to be construed as limiting the sample types applicable to the present invention.

The term "target," when used in reference to a nucleic acid capture, detection, or analysis method, generally refers to a nucleic acid having a feature, e.g., a particular sequence of nucleotides to be detected or analyzed, e.g., in a sample suspected of containing the target nucleic acid. In some embodiments, a target is a nucleic acid having a particular sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "segment" is defined as a region of nucleic acid within the target sequence. The term "sample template" refers to nucleic acid originating from a sample that is analyzed for the presence of a target.

As used herein, the term "locus" refers to a particular position, e.g., of a mutation, polymorphism, or a C residue in a CpG dinucleotide, within a defined region or segment of nucleic acid, such as a gene or any other characterized sequence on a chromosome or RNA molecule. A locus is not limited to any particular size or length, and may refer to a portion of a chromosome, a gene, functional genetic element, or a single nucleotide or basepair. As used herein in reference to CpG sites that may be methylated, a locus refers to the C residue in the CpG dinucleotide.

As used herein, an "inhibitor" means any compound, substance, or composition, or combination thereof, that acts to decrease the activity, precision, or accuracy of an assay, either directly or indirectly, with respect to the activity, precision, or accuracy of the assay when the inhibitor is absent. An inhibitor can be a molecule, an atom, or a combination of molecules or atoms without limitation.

As used herein, the process of passing a mixture through a filter is called "filtration". The liquid produced after filtering a suspension of a solid in a liquid is called "filtrate", while the solid remaining in the filter is called "retentate", "residue", or "filtrand".

As used herein, a "collection liquid" is a liquid in which to place a sample to preserve, stabilize, and otherwise maintain its integrity as a representative sample of the specimen from which the sample was taken. While not limited in the types of compositions that find use as collection liquids, examples of collection liquids are aqueous buffers optionally comprising a preservative and organic solvents, such as acetonitrile.

As used herein, "PVP" refers to polyvinylpyrrolidone, which is a water-soluble polymer made from the monomer N-vinylpyrrolidone. The term PVP is used herein to refer to PVP in various states of cross-linked polymerization, including preparations of PVP that may also be known in the art as polyvinylpolypyrrolidone (PVPP).

As used herein, "insoluble" refers to the property that a substance does not substantially dissolve in water and is essentially immiscible therewith. Upon separation of an aqueous phase from a non-aqueous phase, an insoluble substance does not partition into or partition with the aqueous phase.

As used herein, a "magnet" is a material or object that produces a magnetic field. A magnet may be a permanent magnet or an electromagnet. As used herein, a magnetic particle or bead is responsive to a magnetic field and may be magnetic or paramagnetic.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specfic PCR, inverse PCR (see, e.g., Triglia, et al et al. (1988) Nucleic Acids Res., 16:8186; herein incorporated by reference in its entirety), ligation-mediated PCR (see, e.g., Guilfoyle, R. et al et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985, 557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849, 481, 5,710,264, 5,124,246, and 5,624,802, herein incorporated by reference in their entireties); rolling circle replication (e.g., U.S. Pat. Nos. 6,210,884, 6,183,960 and 6,235, 502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in US Patent Publication US 20090253142 A1 (application Ser. No. 12/404,240), incorporated herein by reference in its entirety for all purposes. Additional amplification plus invasive cleavage detection configurations, termed the QuARTS method, are described in U.S. patent application Ser. Nos. 12/946,737; 12/946,745; and 12/946,752, incorporated herein by reference in their entireties for all purposes.

The term "invasive cleavage structure" as used herein refers to a cleavage structure comprising i) a target nucleic acid, ii) an upstream nucleic acid (e.g., an INVADER oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain).

As used herein, the terms "complementary" or "complementarity" used in reference to polynucleotides (i.e., a sequence of nucleotides) refers to polynucleotides related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally, as in a purified restriction digest, or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like). The primer is typically single stranded for maximum efficiency in amplification, but may alternatively be partially or completely double stranded. The portion of the primer that hybridizes to a template nucleic acid is sufficiently long to prime the synthesis of extension products in the presence of the inducing agent. The exact lengths of the primers will depend on many factors, including temperature, source of primer and the use of the method. Primers may comprise labels, tags, capture moieties, etc.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, amino acids, etc.) in the biopolymer. The sequence (e.g., base sequence) of a nucleic acid is typically read in the 5' to 3' direction.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," and "variant" refer to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment polypeptide are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (e.g., hnRNA); introns may contain regulatory elements (e.g., enhancers). Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the term "kit" refers to any delivery system for delivering materials. In the context of nucleic acid purification systems and reaction assays, such delivery systems include systems that allow for the storage, transport, or delivery of reagents and devices (e.g., inhibitor adsorbants, particles, denaturants, oligonucleotides, spin filters etc. in the appropriate containers) and/or supporting materials (e.g., buffers, written instructions for performing a procedure, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain an materials for sample collection and a buffer, while a second container contains capture oligonucleotides and denaturant. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

Embodiments of the Technology

Although the disclosure herein refers to certain illustrated embodiments, it is to be understood that these embodiments are presented by way of example and not by way of limitation.

Provided herein are methods for isolating DNA, for example from a stool sample. As summarized in FIG. 1, the process comprises homogenizing a sample (e.g., a stool sample) in a suitable buffer and preparing a supernatant from the homogenate. The supernatant is treated with a composition (e.g., a cross-linked polyvinylpyrrolidone (PVP) such as polyvinylpolypyrrolidone (PVPP); see, e.g., U.S. Patent Appln. Ser. No. 61/485,338 to Bruinsma, which is incorporated herein by reference in its entirety) to remove inhibitors and produce a clarified supernatant. DNA in the clarified supernatant is denatured, e.g., by adding guanidine thiocyanate and/or by heating the sample. Then, a target capture reagent, e.g., a magnetic bead to which is linked an oligonucleotide complementary to the target, is added and the solution is incubated under conditions (e.g., ambient temperature for an hour) that promote the association (e.g., by hybridization) of the target with the capture reagent to produce a target:capture reagent complex. After isolating and removing the target:capture reagent complex (e.g., by application of a magnetic field), the resulting solution is heated again to denature the remaining DNA in the clarified supernatant and another target capture reagent can be added to isolate another target. The process can be repeated, to isolate additional targets that are required for the assay or for other purposes. The isolated target:capture reagent complexes from each capture and isolation step are washed and the target DNAs are eluted using a small volume of buffer suitable for downstream analysis.

Moreover, multiple targets can be isolated in each round of isolation by adding multiple target capture reagents to the solution. For example, multiple target capture reagents, each comprising an oligonucleotide specific for a different target can be added to the solution for isolation of multiple targets, then the retained supernatant can be used again for additional, repeated isolation of one or more other targets. It is contemplated that the methods encompass multiple experimental designs that vary both in the number of capture steps and in the number of targets captured in each capture step.

Capture Reagents

In one aspect, the methods provided herein relate to the use of capture reagents. Such reagents are molecules, moieties, substances, or compositions that preferentially (i.e., specifically and selectively) interact with a particular target sought to be isolated and purified. Any capture reagent having desired binding affinity and/or specificity to the analyte target can be used in the present technology. For example, the capture reagent can be a macromolecule such as a peptide, a protein (e.g., an antibody or receptor), an oligonucleotide, a nucleic acid, (e.g., nucleic acids capable of hybridizing with the target nucleic acids), vitamins, oligosaccharides, carbohydrates, lipids, or small molecules, or a complex thereof. As illustrative and non-limiting examples, an avidin target capture reagent may be used to isolate and purify targets comprising a biotin moiety, an antibody may be used to isolate and purify targets comprising the appropriate antigen or epitope, and an oligonucleotide may be used to isolate and purify a complementary oligonucleotide (e.g., a poly-dT oligonucleotide may be used to isolate and purify targets comprising a poly-A tail).

Any nucleic acids, including single-, double-, and triple-stranded nucleic acids, that are capable of binding, or specifically binding, to the target can be used as the capture reagent in the present device. Examples of such nucleic acids include DNA, such as A-, B- or Z-form DNA, and RNA, such as mRNA, tRNA and rRNA, aptamers, peptide nucleic acids, and other modifications to the sugar, phosphate, or nucleoside base. Thus, there are many strategies for capturing a target and accordingly many types of capture reagents are known to those in the art. While not limited in the means by which a target nucleic acid can be captured, embodiments of the technology provided herein comprise using an oligonucleotide that is complementary to the target and that thus captures the target by specifically and selectively hybridizing to the target nucleic acid.

In addition, target capture reagents comprise a functionality to localize, concentrate, aggregate, etc. the capture reagent and thus provide a way to isolate and purify the target when captured (e.g., bound, hybridized, etc.) to the capture reagent, i.e., when a target:capture reagent complex is formed. For example, in some embodiments the portion of the target capture reagent that interacts with the target (e.g., the oligonucleotide) is linked to a solid support (e.g., a bead, surface, resin, column, and the like) that allows manipulation by the user on a macroscopic scale. Often, the solid support allows the use of a mechanical means to isolate and purify the target:capture reagent complex from a heterogeneous solution. For example, when linked to a bead, separation is achieved by removing the bead from the heterogeneous solution, e.g., by physical movement. In embodiments in which the bead is magnetic or paramagnetic, a magnetic field is used to achieve physical separation of the capture reagent (and thus the target) from the heterogeneous solution. Magnetic beads used to isolate targets are described in the art, e.g., as described in European Patent Application No. 87309308, incorporated herein in its entirety for all purposes.

EXAMPLES

Example 1

During the development of embodiments of the technology provided herein, it was demonstrated that the majority of the DNA for a given target is depleted from a stool supernatant in a single isolation. The isolation was performed according to the flow chart shown in FIG. 1. After final elution, the recoveries of the two targets (Gene A and Gene V) from isolations 1 and 2 were monitored by SYBR Green qPCR assays using 1 microliter of eluate in a 25-microliter volume reaction. For both targets, isolation 1 yielded good recovery of target, whereas the eluate from isolation 2 failed to produce any qPCR signal for either target (FIG. 2).

Example 2

Figure 3:
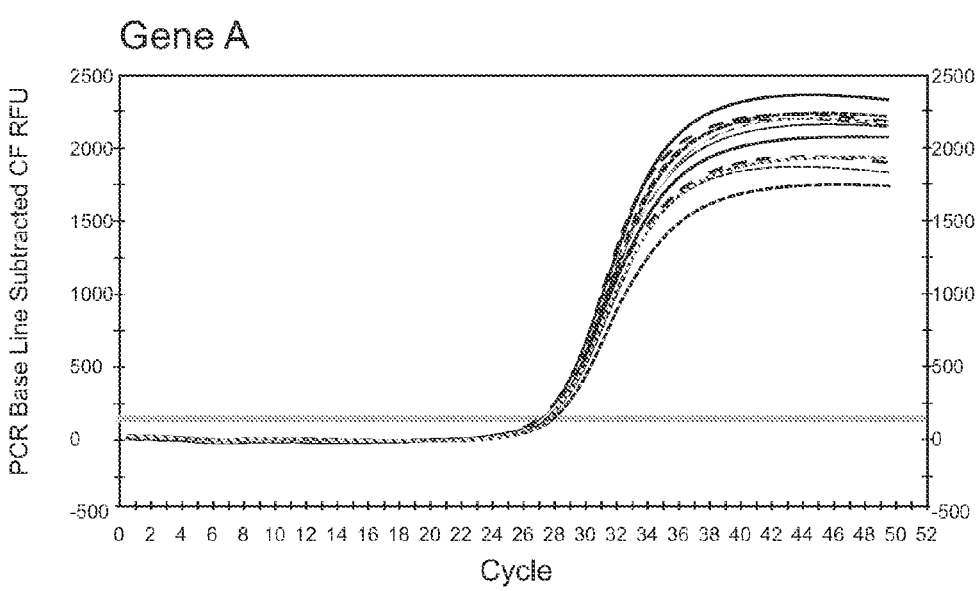
FIGS. 3A-3D show plots showing the results of quantitative PCRs in which the recoveries of four target DNAs are similar regardless of the order in which the four target DNAs are extracted from a stool sample.
Figure 3:
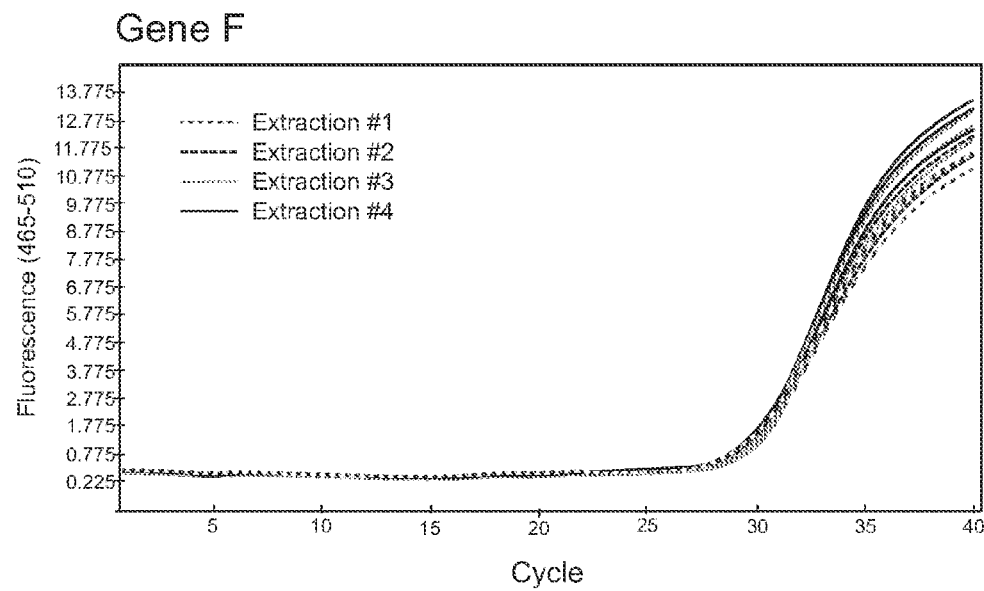

During the development of embodiments of the technology provided herein, it was demonstrated that DNA isolation can be performed repeatedly on a single sample through a minimum of four cycles of denaturation and hybridization without compromising the integrity of the human DNA in the stool supernatant. In this example, four targets (Genes A, F, V, and W) were captured from the sample and the order of their capture was varied. After elution, the recovery of each target was monitored by SYBR Green qPCR. In FIG. 3, plots show the amplification curves for each gene when it was captured first, second, third, and fourth in the sequence of isolations. The superposition of the amplification curves demonstrates that recoveries were approximately equal regardless of the order of isolation. Table 1 quantifies the results from FIG. 3.

TABLE 1

| Target | Isolation | Mean $C_p$ | Mean Strands/μL |
| --- | --- | --- | --- |
| Gene A | #1 | 28.92 | 862 |
|  | #2 | 28.89 | 878 |
|  | #3 | 28.85 | 907 |
|  | #4 | 28.73 | 984 |
| Gene F | #1 | 29.32 | 499 |
|  | #2 | 29.36 | 489 |
|  | #3 | 29.29 | 511 |
|  | #4 | 29.01 | 614 |

TABLE 1-continued

| Target | Isolation | Mean $C_p$ | Mean Strands/µL |
|---|---|---|---|
| Gene V | #1 | 31.29 | 129 |
| | #2 | 31.01 | 155 |
| | #3 | 31.18 | 139 |
| | #4 | 30.84 | 177 |
| Gene W | #1 | 29.17 | 724 |
| | #2 | 29.11 | 757 |
| | #3 | 28.99 | 819 |
| | #4 | 29.16 | 730 |

For all four genes, the mean $C_p$ (Crossing point—the cycle number at which the amplification curve crosses a fixed threshold) and strand numbers were essentially equal regardless of the order of extraction.

Example 3

Exemplary Procedure for Serial Isolation of a Plurality of Target Nucleic Acids

Figure 2:
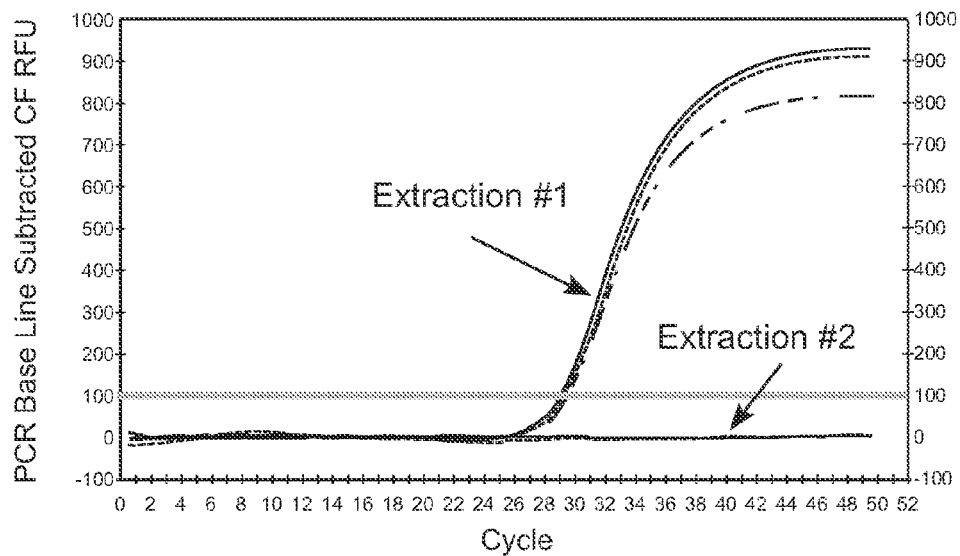
FIG. 2A is a plot showing the results of a quantitative PCR in which a single extraction from a stool sample recovers most of the target DNA.
FIG. 2B shows the concentrations of Gene A and Gene V in nucleic acid solutions from a first extraction and a second extraction.

As Diagrammed in FIG. 1:
1. A stool sample is homogenized, e.g., with a buffer, to form a stool homogenate. The homogenate treated to partition residual solids from the fluid, e.g., by centrifugation or filtration, to produce a "stool supernatant."
2. Stool supernatant is treated to remove assay inhibitors (e.g., with polyvinylpolypyrrolidone, as described in U.S. Pat. Appl. Ser. No. 61/485,338, which is incorporated herein by reference in its entirety), producing "clarified supernatant".
3. Ten milliliters of clarified supernatant (representing an equivalent of approximately 4 grams of stool) is mixed with guanidine thiocyanate (GTC) to a final concentration of 2.4 M;
4. The mixture is then heated in a 90° C. water bath for 10 minutes to denature the DNA (and proteins) present in the stool.
5. Paramagnetic particles containing covalently attached (coupled) oligonucleotides complementary to the target sequence(s) of interest ("target-specific capture probes") are added to the sample. The sample is then incubated (e.g., at ambient temperature, about 22-25° C.) for one hour to enable hybridization of the target DNA to the capture probes on the magnetic particles.
6. The mixture of clarified supernatant, GTC, and particles is exposed to a magnetic field to separate the particles (now containing target DNA hybridized to the capture probes) from the stool supernatant/GTC mixture, which is transferred to a new tube. See, e.g., U.S. patent application Ser. No. 13/089,116, which is incorporated herein by reference.
7. The paramagnetic particles are then washed and the target DNA eluted, ready for use in detection assays.
8. The supernatant/GTC mixture retained in step 6 is returned to the 90° C. water bath for 10 minutes to repeat denaturation (step 4). Step 5 is then repeated by adding magnetic particles containing capture probes complementary to different targets DNAs, and the hybridization, particle separation and elution steps are repeated to produce a purified sample of a second DNA target.

The denaturation/hybridization/separation cycle (steps 4-6) can be repeated at least four or more times to serially extract different target DNAs from the same stool supernatant sample.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in related fields (e.g., engineering, mechanics, materials science, or medical diagnostics) are intended to be within the scope of the following claims.

We claim:

1. A composition comprising a residual supernatant from a human stool homogenate comprising human DNA and DNA from gut-resident bacteria, said residual supernatant produced by a method comprising:
   i) preparing a stool supernatant fluid from said human stool homogenate, wherein said stool supernatant fluid is produced by homogenizing a human stool sample with a buffer to produce said human stool homogenate, and treating said human stool homogenate to partition residual solids from a fluid fraction, wherein said fluid fraction is said stool supernatant fluid;
   ii) treating the stool supernatant fluid with insoluble polyvinylpolypyrrolidone to adsorb and remove assay inhibitors, and removing said insoluble polyvinylpolypyrrolidone to produce treated stool supernatant fluid,
   iii) adding guanidine thiocyanate to said treated stool supernatant fluid to a concentration of 2-3 M guanidine thiocyanate;
   iv) exposing treated stool supernatant fluid comprising guanidine thiocyanate to a plurality of different target-specific capture reagents, under conditions wherein each of said plurality of different target-specific capture reagents forms a complex with a different target human DNA, wherein each target-specific capture reagent comprises an oligonucleotide covalently attached to a particle, said oligonucleotide complementary to at least a portion of a target human DNA, and wherein said exposing comprises incubating said treated stool supernatant fluid comprising guanidine thiocyanate with said target-specific capture reagents to produce target-specific capture reagent/target human DNA complexes, and
   v) removing target-specific capture reagent/target human DNA complexes from said treated stool supernatant fluid to produce said residual supernatant,
      wherein said residual supernatant is treated stool supernatant fluid from which target-specific capture reagent/target human DNA complexes have been removed, said residual supernatant comprising guanidine thiocyanate, said DNA from gut-resident bacteria, and human DNAs not complementary to the oligonucleotides of the target-specific capture reagents used in step iv).

2. The composition of claim 1, wherein said particles are magnetic particles.

3. The composition of claim 1, wherein said stool homogenate comprises at least 4 grams of stool from a human subject.

4. The composition of claim 1, wherein prior to step iv), said method comprises heating said treated stool supernatant fluid.

5. The composition of claim 4, wherein said heating comprises heating to 90° C.

6. The composition of claim 1, wherein said polyvinylpyrrolidone is polyvinylpolypyrrolidone.

7. The composition of claim 1, wherein said plurality of different target-specific capture reagents comprises at least 3 different target-specific capture reagents.

8. The composition of claim 1, wherein said plurality of different target-specific capture reagents comprises at least 4 different target-specific capture reagents.

9. The composition of claim 1, wherein one or more of said target human DNAs are from genes associated with a disease state selected from the group consisting of colorectal cancer and colorectal adenoma.

* * * * *